(12) United States Patent
Dobrovolny

(10) Patent No.: US 6,602,190 B2
(45) Date of Patent: Aug. 5, 2003

(54) MULTI-POSITION SPHERICAL RETRACTOR HOLDER

(75) Inventor: Walter Dobrovolny, St. Paul, MN (US)

(73) Assignee: Minnesota Scientific, Inc., St. Paul, MN (US)

( * ) Notice: Subject to any disclaimer, the term of this patent is extended or adjusted under 35 U.S.C. 154(b) by 0 days.

(21) Appl. No.: 09/943,794

(22) Filed: Aug. 31, 2001

(65) Prior Publication Data

US 2002/0177753 A1 Nov. 28, 2002

Related U.S. Application Data

(60) Provisional application No. 60/293,594, filed on May 25, 2001.

(51) Int. Cl.[7] ............................................... A61B 17/02
(52) U.S. Cl. ....................................... 600/234; 600/231
(58) Field of Search ................................ 600/227, 228, 600/229, 231, 232, 233, 235; 269/257, 268, 269, 270

(56) References Cited

U.S. PATENT DOCUMENTS

| | | | | |
|---|---|---|---|---|
| 324,907 A | * | 8/1885 | Wilder | 269/268 |
| 2,608,192 A | * | 8/1952 | Heitmeyer et al. | 248/279.1 |
| 3,509,873 A | * | 5/1970 | Carlin | 600/226 |
| 4,424,724 A | | 1/1984 | Bookwalter et al. | 74/540 |
| 4,457,300 A | * | 7/1984 | Budde | 600/228 |
| 4,573,452 A | * | 3/1986 | Greenberg | 600/102 |
| 4,616,632 A | * | 10/1986 | Wigoda | 600/227 |
| 4,617,916 A | | 10/1986 | LeVahn et al. | 128/20 |
| 4,726,356 A | | 2/1988 | Santilli et al. | 128/20 |
| 4,727,872 A | | 3/1988 | Hawk | 128/207.14 |
| 4,971,038 A | | 11/1990 | Farley | 128/20 |
| 4,989,587 A | | 2/1991 | Farley | 128/20 |
| RE34,150 E | | 12/1992 | Santilli et al. | 128/20 |
| 5,375,481 A | | 12/1994 | Cabrera et al. | 74/577 |
| 5,876,332 A | * | 3/1999 | Looney | 600/102 |
| 5,876,333 A | | 3/1999 | Bigliani et al. | 600/231 |
| 6,007,486 A | | 12/1999 | Hunt et al. | 600/205 |
| 6,013,027 A | * | 1/2000 | Khan et al. | 600/201 |
| 6,063,021 A | | 5/2000 | Hossain et al. | 600/37 |
| 6,083,154 A | | 7/2000 | Liu et al. | 600/234 |
| 6,322,500 B1 | * | 11/2001 | Sikora et al. | 600/219 |

* cited by examiner

Primary Examiner—Cary E. O'Connor
(74) Attorney, Agent, or Firm—Kinney & Lange, P.A.

(57) ABSTRACT

A device for securing a retractor to a support arm, the retractor including a handle and a blade, the device includes a spheroidal member having a through bore adapted to engage the handle of the retractor where the spheroidal member is rotatably captivated within a spheroidal member retaining portion of a main member of a housing of the device. The housing also includes a retaining member operably attached to the main member where the main member and the retaining member cooperate to engage the support arm. A tightening mechanism is operably attached to the main member and is in communication with the retaining member. The tightening mechanism is positionable between a first position wherein the spheroidal member is rotatably positionable within the spheroidal member retaining portion and a second position where in the tightening mechanism causes a first frictional engagement between the spheroidal member and the spheroidal member retaining portion such that the spheroidal member is fixed in first selected position.

90 Claims, 11 Drawing Sheets

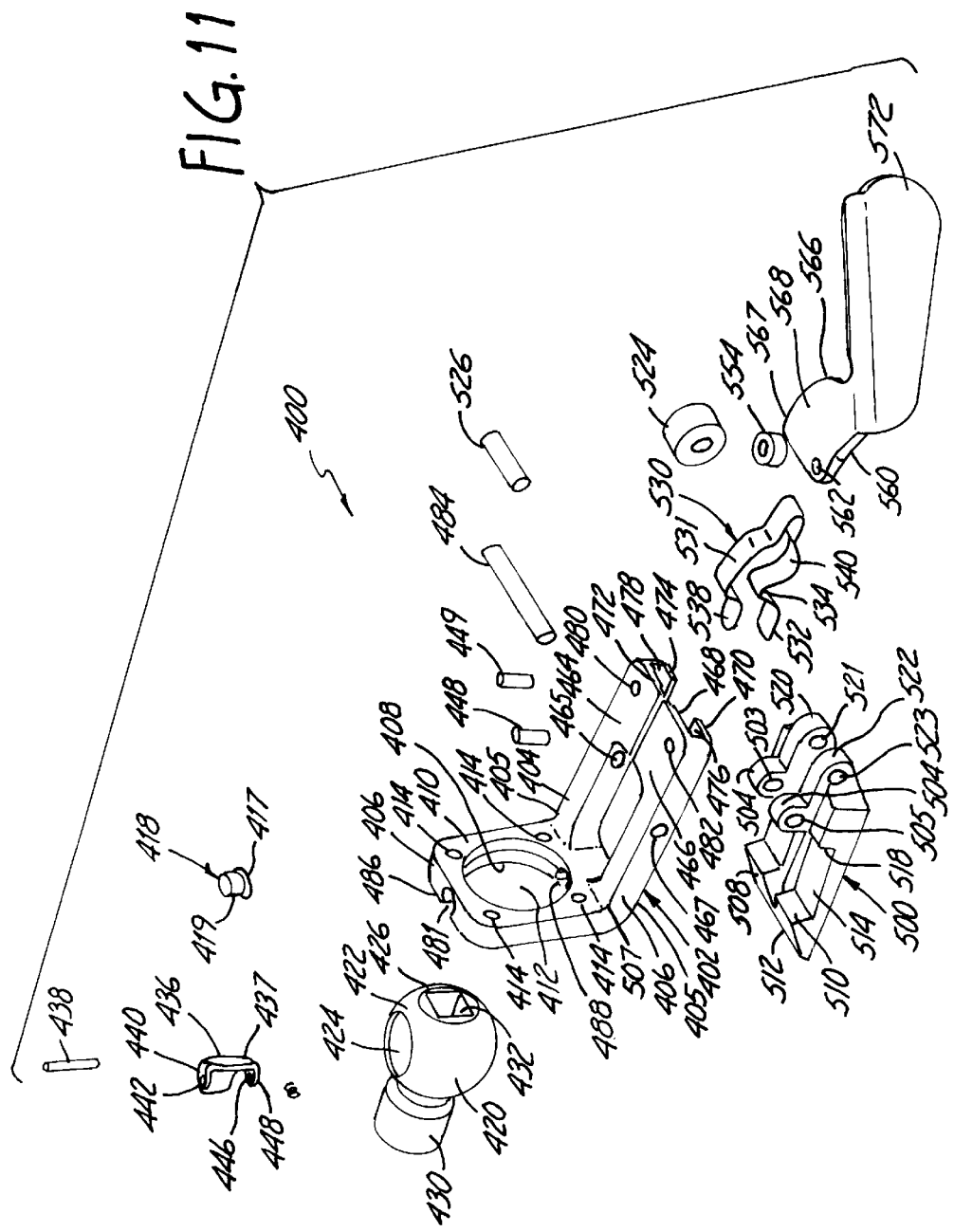

MULTI-POSITION SPHERICAL RETRACTOR HOLDER

BACKGROUND OF THE INVENTION

The present invention generally relates to a surgical retractor clamp. More particularly, the present invention relates to a retractor clamp which allows a retractor blade to be positioned in three dimensions by manipulating the retractor within the retractor clamp.

The location of retractors is critical in gaining access to a surgical site prior to performing a surgical procedure. In order to gain access to a surgical site several retractors may be required at different angles, elevations and depths. Retractor clamps or holders which provide for multiple positional adjustment of retractors aid the surgeon in preparing the surgical site for the surgical procedure.

Prior to providing retractor clamps or holders with positional adjustment, the position of a retractor support was adjusted to reposition a retractor at a surgical site. Retractor supports are typically rigid members, therefore when a retractor support is repositioned, all of the retractors attached to the retractor support were also repositioned. In some instances, a surgeon may only want to reposition a single retractor on a support arm while maintaining the position of the other retractors on the support arm to gain better access to a surgical site. Without providing for positional adjustment of the retractor at the clamp or holder, individual positioning of retractors is not feasible.

Retractor clamps or holders in the prior art provided height and depth adjustment by the use of racheting mechanisms. Cabrera et al. U.S. Pat. No. 5,375,481 discloses a racheting mechanism for adjusting the height of a retractor blade. Additionally, the retractor holder disclosed in the Cabrera et al. patent discloses a through bore and a pawl cooperating with aligned teeth on the retractor handle to adjust the distance of a retractor blade from the retractor support.

Bookwalter et al. U.S. Pat. No. 4,424,724 also discloses a retractor holder which vertically adjusts by manipulating a racheting mechanism. A depth of a retractor is positionable by the cooperation of aligned teeth on the retractor handle with a through bore of a complementary cross section and a spring biased pawl.

Santilli et al. U.S. Pat. Nos. 4,726,356 and Re. 34,150 disclose a retractor which is positionable along a length of a retractor support having aligned teeth. A handle having extending pins meshes with the aligned teeth to create a rack and pinion system to adjust the position of the retractor along the support arm.

Other surgical retractors provide for rotational movement of a retractor, typically with a ball and socket articulated joint. Examples of retractor clamps or holders providing for rotational movement include Lei et al. U.S. Pat. No. 6,083,154, Hunt et al. U.S. Pat. No. 6,007,486 and Hossain et al. U.S. Pat. No. 6,0764,021.

BRIEF SUMMARY OF THE INVENTION

The present invention includes a device for securing a retractor to a support arm, the retractor including a handle and a blade, the device includes a spheroidal member having a through bore adapted to engage the handle of the retractor where the spheroidal member is rotatably captivated within a spheroidal member retaining portion of a main member of the housing of the device. The housing also includes a retaining member operably attached to the main member where the main member and the retaining member cooperate to engage the support arm. A tightening mechanism is operably attached to the main member and is in communication with the retaining member. The tightening mechanism is positionable between a first position wherein the spheroidal member is rotatably positionable within the spheroidal member retaining portion and a second position wherein the tightening mechanism causes a first frictional engagement between the spheroidal member and the spheroidal member retaining portion such that the spheroidal member is fixed in a first selected position.

BRIEF DESCRIPTION OF THE DRAWINGS

FIG. 11 is an alternative exploded perspective view of the third alternative embodiment of the present invention.

DETAILED DESCRIPTION

Figure 1:
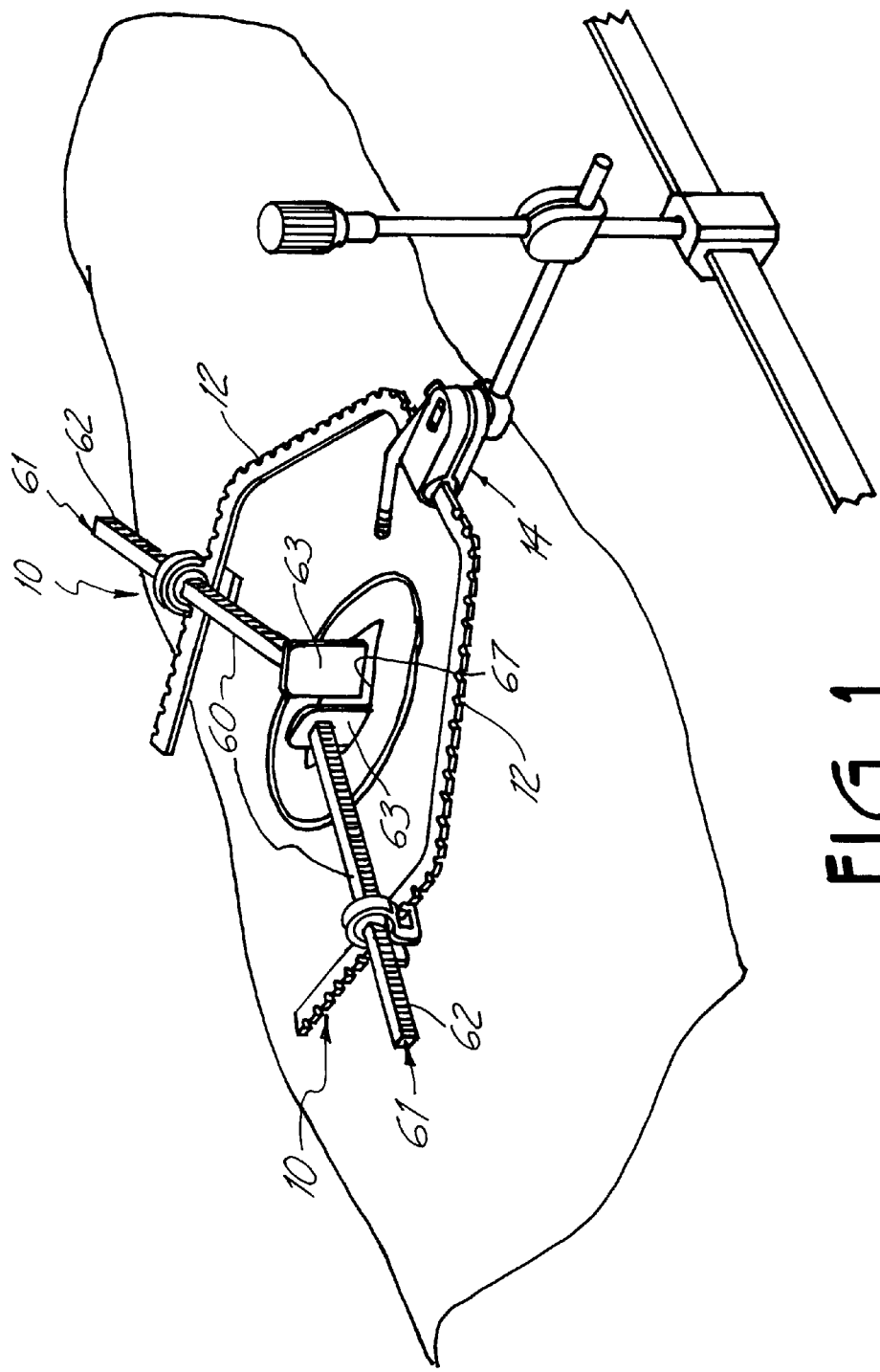
FIG. 1 is a perspective view of a first alternative embodiment of the clamping device of the present invention attached to a retractor support attached to a side rail of a surgical table.

The clamping device of the present invention is generally illustrated in FIG. 1 at 10. The clamping device 10 engages a rectangular cross-sectional support arm 12 and provides a retractor blade adjustment in three dimensions. A clamping device 14 for positioning the support arms 12 is disclosed in U.S. Pat. No. 4,617,916 which is hereby incorporated by reference.

Figure 2:
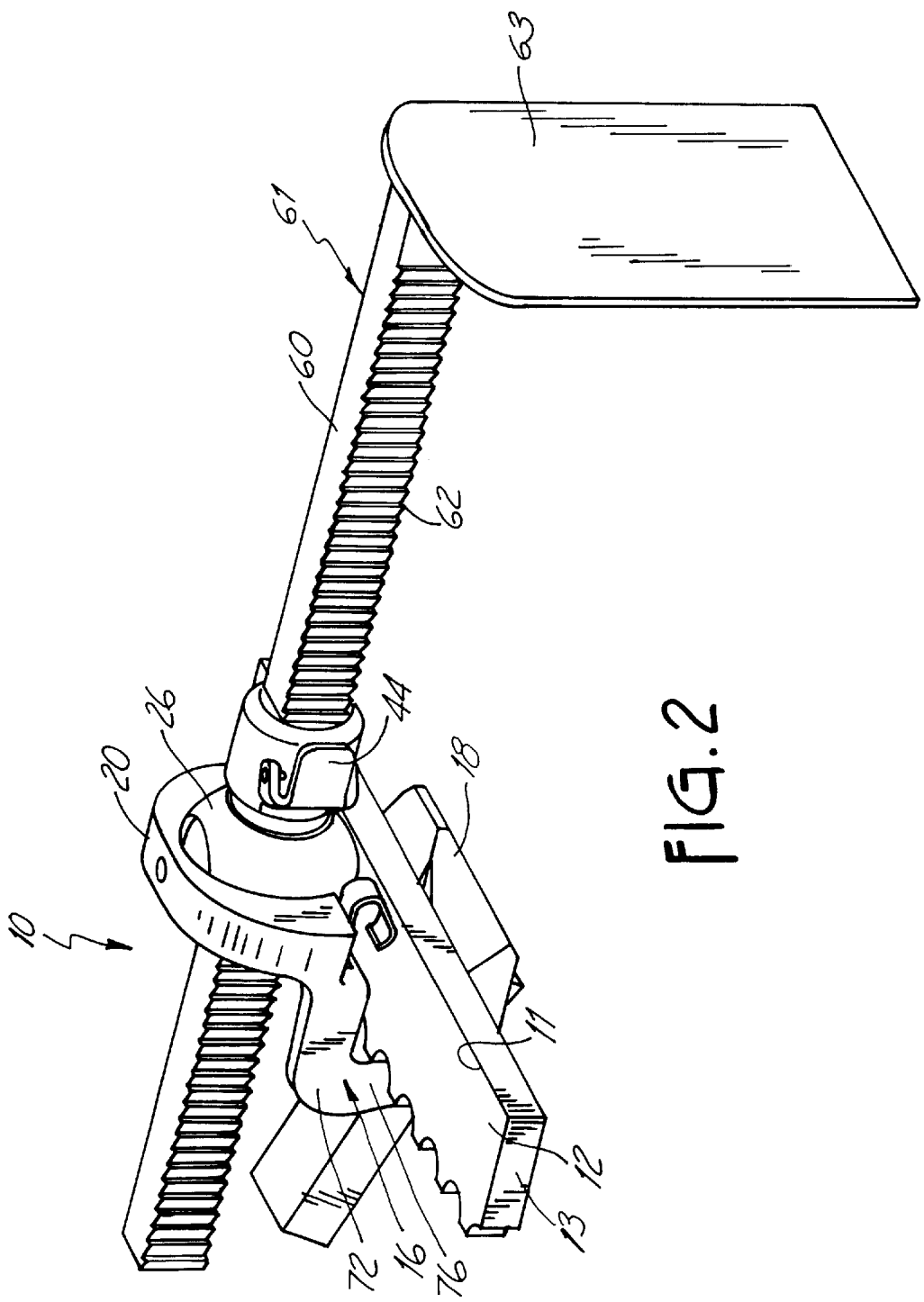
FIG. 2 is a perspective view of the first alternative embodiment the clamping device of the present invention.
Figure 3:
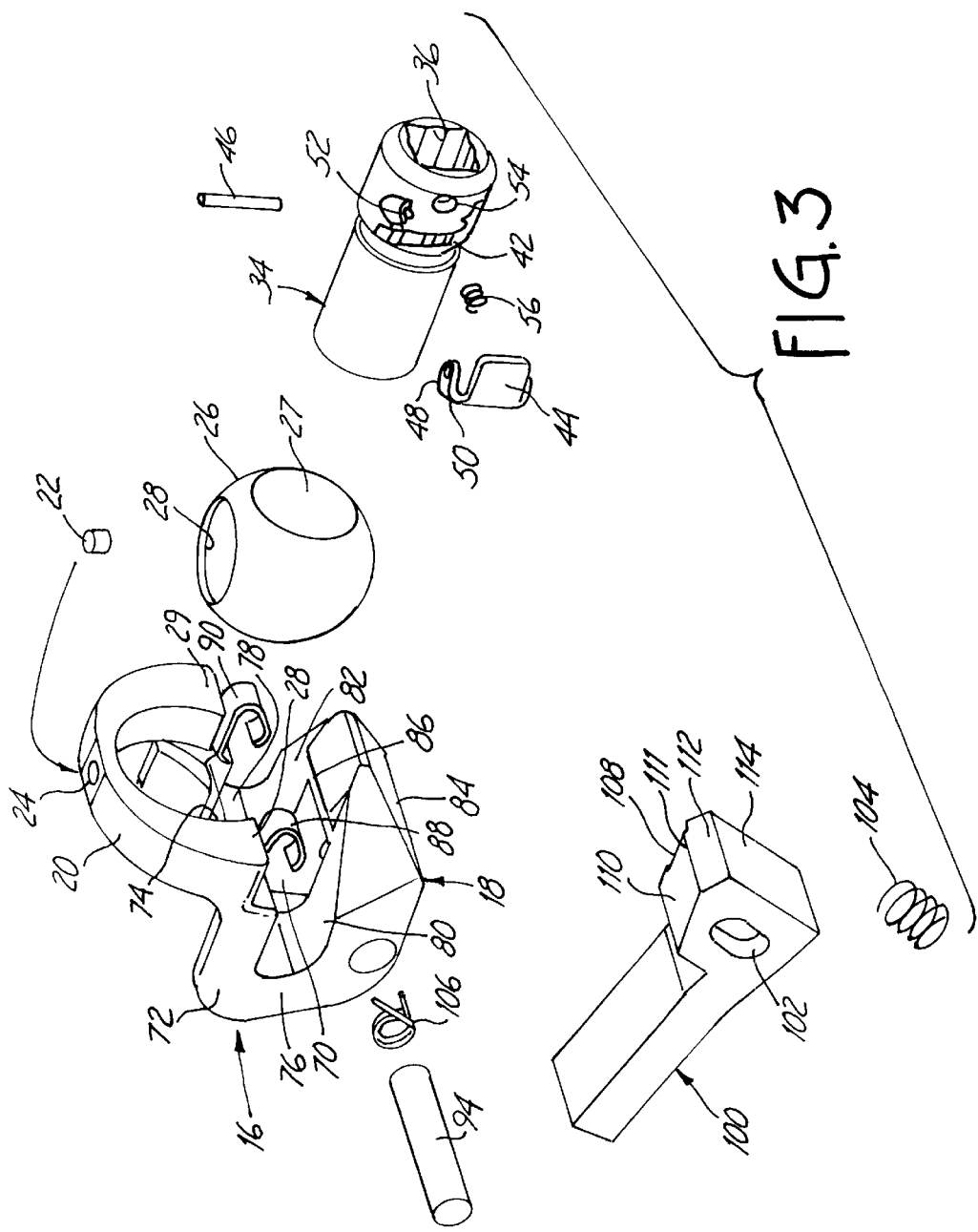
FIG. 3 is an exploded perspective view of the first alternative embodiment of the clamping device of the present invention.
Figure 4:
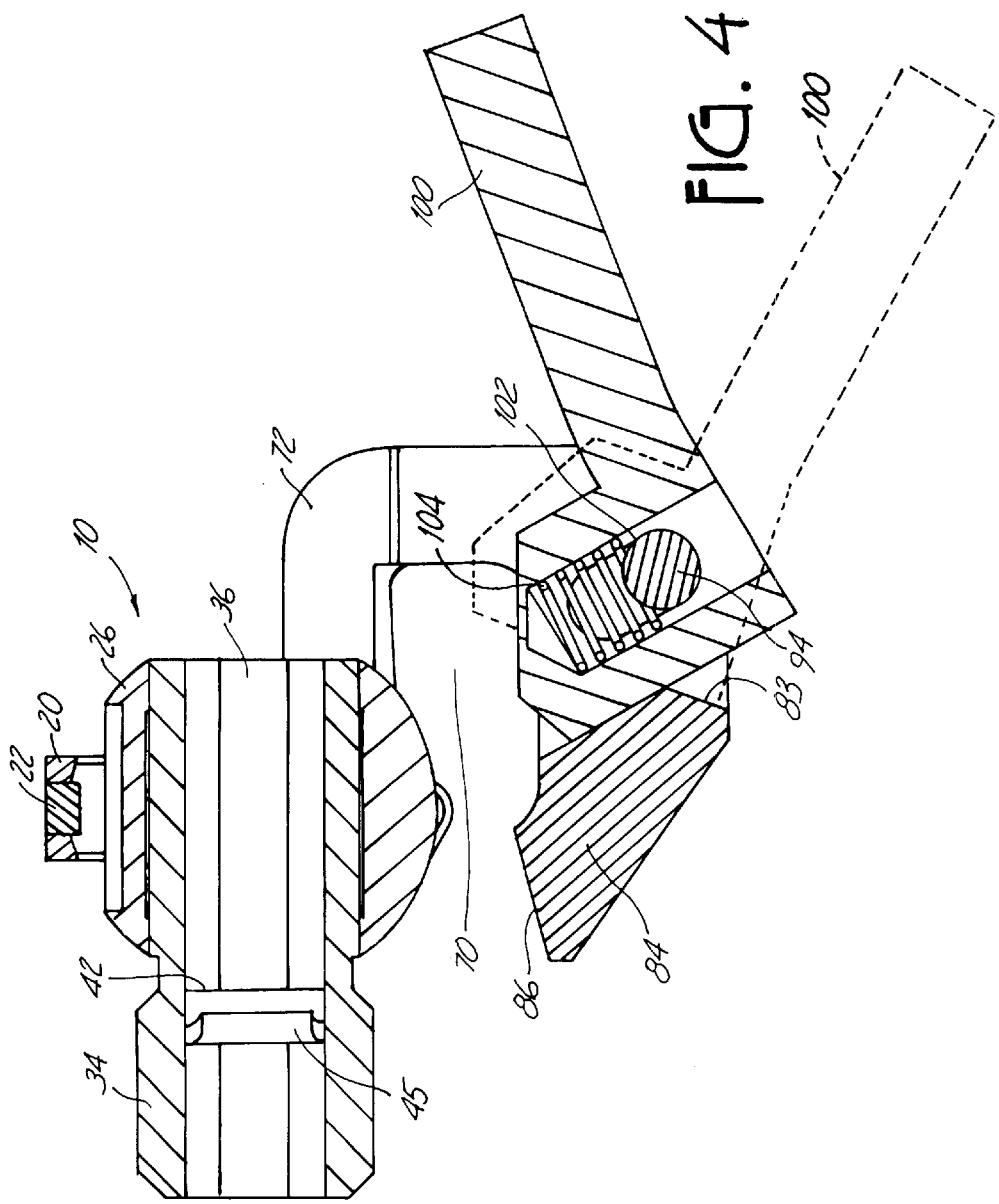
FIG. 4 is a sectional view of the first alternative embodiment of the clamping device of the present invention.

Referring to FIGS. 2–4, the retractor clamp 10 of the present invention includes a housing 16 having a main body 18 and an arcuate upper portion 20. The arcuate upper portion 20 cooperates with a spherical member 26. An opening at a bottom of the arcuate upper portion 20 is smaller than a diameter of the spherical member 26 thereby retaining the spherical member 26 within the arcuate upper portion 20. Although the embodiment discloses a spherically shaped member 26, other geometric shaped members are within the scope of the invention including spheroidal configurations. What is meant by spheroidal is objects having portions of the outer surface which are arcuate although the portion of the outer surface need not be defined by a consistent radial distance from a center of the member such as ellipsoids.

The spherical member 26, positioned within the arcuate upper portion 20, includes a cavity 28 in an upper region which cooperates with a pin 22 disposed through an aperture 24 at a top portion of the arcuate upper portion 20. The pin 22 extends into the cavity 28 in the upper region of the spherical member 26 thereby limiting the rotation of the spherical member 26 within the arcuate portion 20. The pin 22 within the cavity 28 also prevents the spherical member 26 from accidentally disengaging the arcuate upper portion 20.

Figure 7:
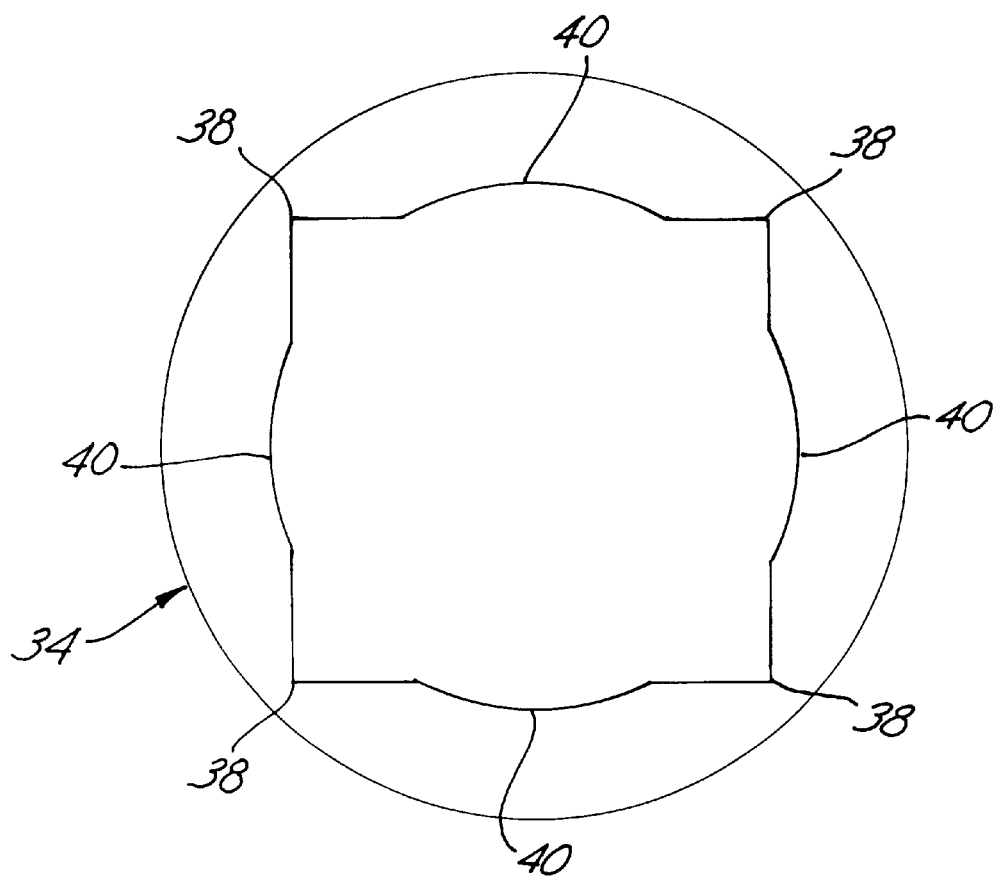
FIG. 7 is a sectional view of the retractor handle engaging member of the present invention.

A retractor handle engaging member 34 is positioned within a complimentary through bore 27 in the spherical member 26 and is secured therein, preferably by a weld. The retractor handle engaging member includes a through bore 36 extending therethrough. Referring to FIG. 7, the through bore 36 includes four square corners 38 and side members 40 having arcuate mid-portions. The through bore 36, having four square corners 38 and side members 40 having arcuate mid-portions, allows the retractor handle engaging member 34 to accept both square cross-sectional retractor handles and circular cross-sectional retractor handles. Although the preferred embodiments disclose a through bore having square corners and arcuate mid portions, other cross-sectional configurations are within the scope of the invention including any polygon cross-sectional retractor clamp. Additionally, a through bore including a plurality of arcuate portions separated by straight lines forming obtuse angles is within the scope of the invention.

Referring to FIGS. 3 and 4, the retractor handle engaging member 34 also includes a slot 42 which intersects the through bore 36. A pawl 44 is pivotally attached to the retractor handle engaging member 34 by a pin 46 extending through a first tab 48 of the pawl 44 where the first tab 48 includes an aperture 50, a through bore 52 in a side of the retractor handle engaging member 34 and a second aperture (not shown) in a second tab (not shown) which is aligned with the first aperture 50 in the first tab 48. The retractor handle engaging member 34 also includes an invention 54 which accepts a coil spring 56. The coil spring 56 biases the pawl 44 such that an end 45 of the pawl 44 is disposed through the slot 42 and within the through bore 36 in the retractor handle engaging member 34.

Referring to FIGS. 1 and 2, a retractor handle 60 having aligned slanted teeth 62 along a length of the handle 60 is disposed within the through bore 36 in the retractor handle engaging member 34. The pawl 44 cooperates with the slanted teeth 62 to allow the retractor handle 60 to be inserted into the through bore 36 while preventing the retractor handle from being removed from the through bore 36. The retractor handle 60 is removed from the through bore 60 by overcoming the bias of the spring 56 to position the end 45 of the pawl 44 outside of the through bore 36 thereby disengaging the pawl 44 from the slanted teeth 62 of the retractor handle 60.

The main body 18 of the housing 16 includes a C-shaped slot 70 which cooperates with and slidably engages the support arm 12. The C-shaped slot is defined by first and second top portions 72, 74 extending from first and second ends 28, 29 of the arcuate upper portion 20; first and second back portions 76, 78; and first and second bottom portions 80, 82, all respectively. The bottom portions 80, 82 are connected by a tapered portion 84 having an upwardly extending ramp 86 on an upper surface where the ramp 86 contacts a bottom surface 13 of the support arm 12. The main body 18 includes first and second arcuate spring members 88, 90 which are attached to the top portions 72, 74 proximate the first and second ends 28, 29 of the arcuate portion 20.

The first and second top portions 72, 74, back portions 76, 78 and bottom portions 80, 82, all respectively, are spaced apart to define a channel which intersects the C-shaped slot 70 and accepts a toggle lever 100. The first and second bottom portions 80, 82 include aligned apertures (one of which is shown) 92 which cooperate with an elongated slot 102 in the toggle lever 100. A pin 94 is inserted through the first and second apertures in the bottom portions 80, 82 and the elongated slot 102 in the toggle lever 106 to provide a pivotal engagement between the housing 16 and the toggle lever 100. A compression spring 104 is positioned within the elongated slot 102 above the pin 94 to bias the toggle lever 100 into the C-shaped slot 70.

Referring to FIG. 3, a coil spring 106 is positioned within a groove 108 in the toggle lever 100 aligned with the elongated slot 102 and is disposed about the pin 94. The coil spring 106 biases the toggle lever 100 in an upward direction.

The toggle lever 100 includes a first engaging surface 110 and a second engaging surface 112. The first engaging surface 110 extends beyond an axis extending through a center of the elongated slot 102 in the toggle lever 100. The second engaging surface 112 is angled upward from a first end 114 of the toggle lever 100 such that the first and second engaging surfaces 110, 112 meet at a common line 111.

In operation, the toggle lever 100 is positioned between a first position and a second position as illustrated in FIG. 4 where the toggle lever 100 is shown in the second position by dashed lines. When the toggle lever 100 is in the first position, a top surface 11 of the support arm 12 contacts the first and second top portions 70, 72 of the frame 16 and the first and second arcuate spring members 88, 90. The ramp 86 and the first engaging surface 110 are adjacent to the bottom surface 13 of the support arm 12. With the toggle lever 100 in the first position, the retractor clamp 10 is slidably positionable along the support arm 12 and the spherical member 26 is hemispherically rotatable within the arcuate portion 20 thereby allowing the operator of a retractor 61 to position a retractor blade 63 in a selected position. What is meant by hemispherically rotatable is that the spherical member is able to rotate such that the retractor is positionable at any point along a surface of a hemisphere.

When the retractor blade 63 is in the selected position, the toggle lever 100 is rotated downward until the first end 114 of the toggle lever 100 contacts a surface 83 of the tapered portion 86 which limits the rotation of the toggle lever 100. When the toggle lever 100 is in the second position, the second engaging surface 112 is displaced into the C-shaped slot 70. The second engaging surface 112 contacts the bottom surface 13 of the retractor support arm 12 and applies an upward force to the bottom surface 13 of the support arm 12. The upward force provided by the toggle lever 100 on the support arm 12 forces the support arm 12 in an upwards direction which compresses the first and second arcuate springs 88, 90 and forces the spherical member 26 upward and into a first frictional engagement between the arcuate surface 20 and the top surface 11 of the support member 12. The first frictional engagement secures the spherical member 26 in a selected position.

The housing 16 is secured to the support arm 12 by a second frictional engagement of the support arm 12 between the first and second arcuate spring members 88, 90 and the first and second top portions 70, 72 contacting the upper surface 11 of the support arm 12 and the second engaging surface 112 of the toggle lever 100 and the ramp 86 contacting the bottom surface 13 of the support arm 12. The elongated slot 102 allows the toggle lever 100 to move slightly downward while the compression spring 104 within the elongated slot 102 maintains a constant force on the support arm 12 thereby retaining the retractor clamp 10 in the selected position.

The ramp 86 provides support to a front portion of the retractor support arm 12. The ramp 86 prevents the support arm 12 from slanting downward at the front portion when the toggle lever 100 applies the upward force to a back portion of the support arm 12.

With the retractor clamp 10 in the second position, the operator of the retractor clamp 10 can further position the retractor blade 63 by pulling the retractor handle 60 having the aligned slanted teeth 62 away from the surgical site 67. The pawl 44 engages the teeth 62 in the retractor handle 60 and prevents the retractor blade 63 from moving in the opposite direction towards the surgical site 67.

When the surgical procedure is completed, the operator disengages the pawl 44 from the teeth 62 in the retractor handle 60 by overcoming the bias applied to the pawl 44 by the spring 56. When the pawl 44 is disengaged from the teeth 62, the retractor blade 63 is positioned towards the surgical site 67 which removes pressure applied by the retractor 61 to the patient. Once the pressure has been removed from the retractor blade 63, the toggle lever 100 is positioned into the first position which releases the first and second frictional engagements. With the first and second frictional engagements released, the operator can reposition the clamp 10 on the support arm 12 or remove the retractor clamp 10 from the support arm 12.

Although the embodiment 10 is shown retaining a retractor on a support arm, it is also within the scope of the invention that the clamp of the present invention be used to clamp two support members to each other.

Figure 5:
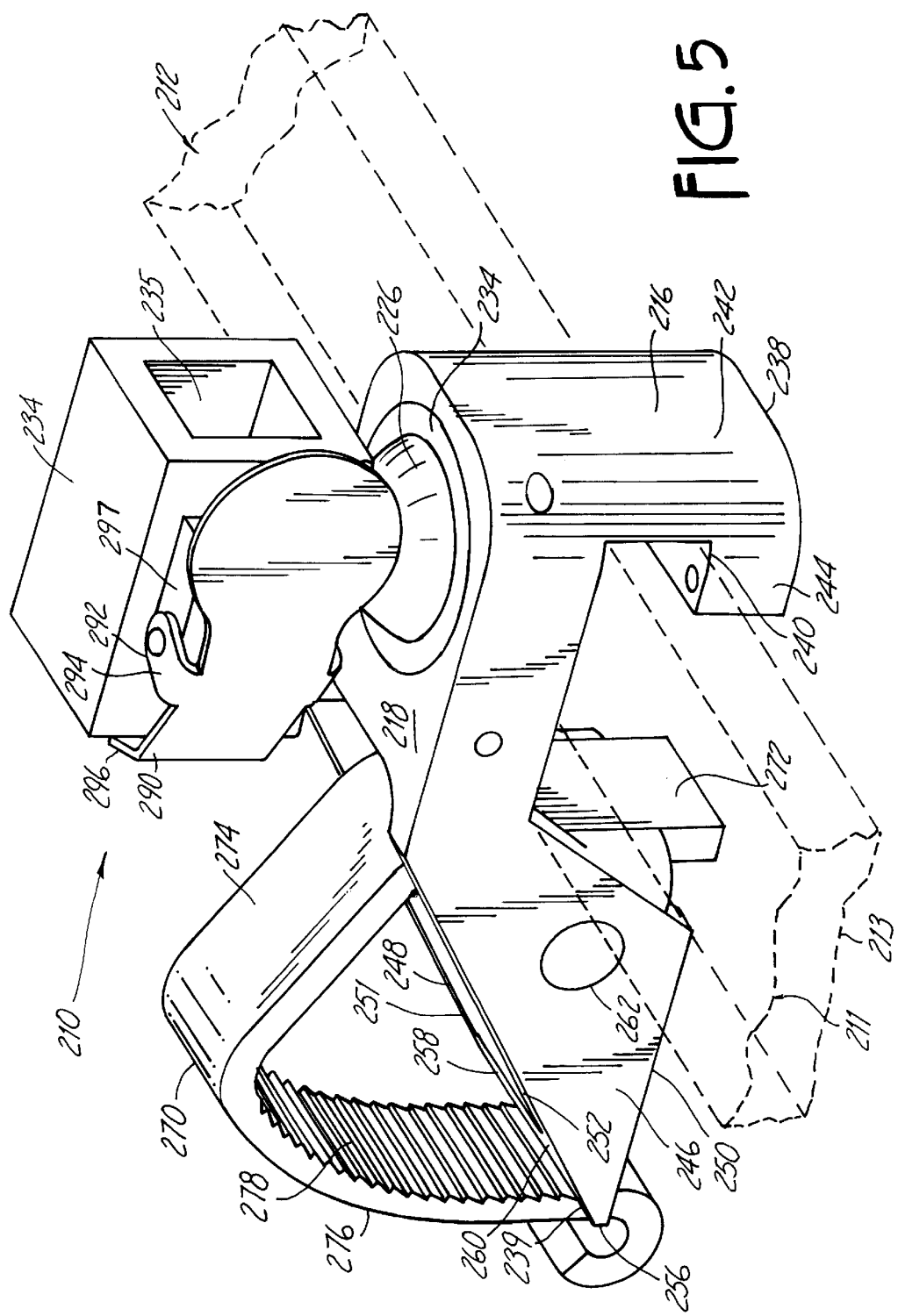
FIG. 5 is a perspective view of a second alternative embodiment of the clamping device of the present invention.
Figure 6:
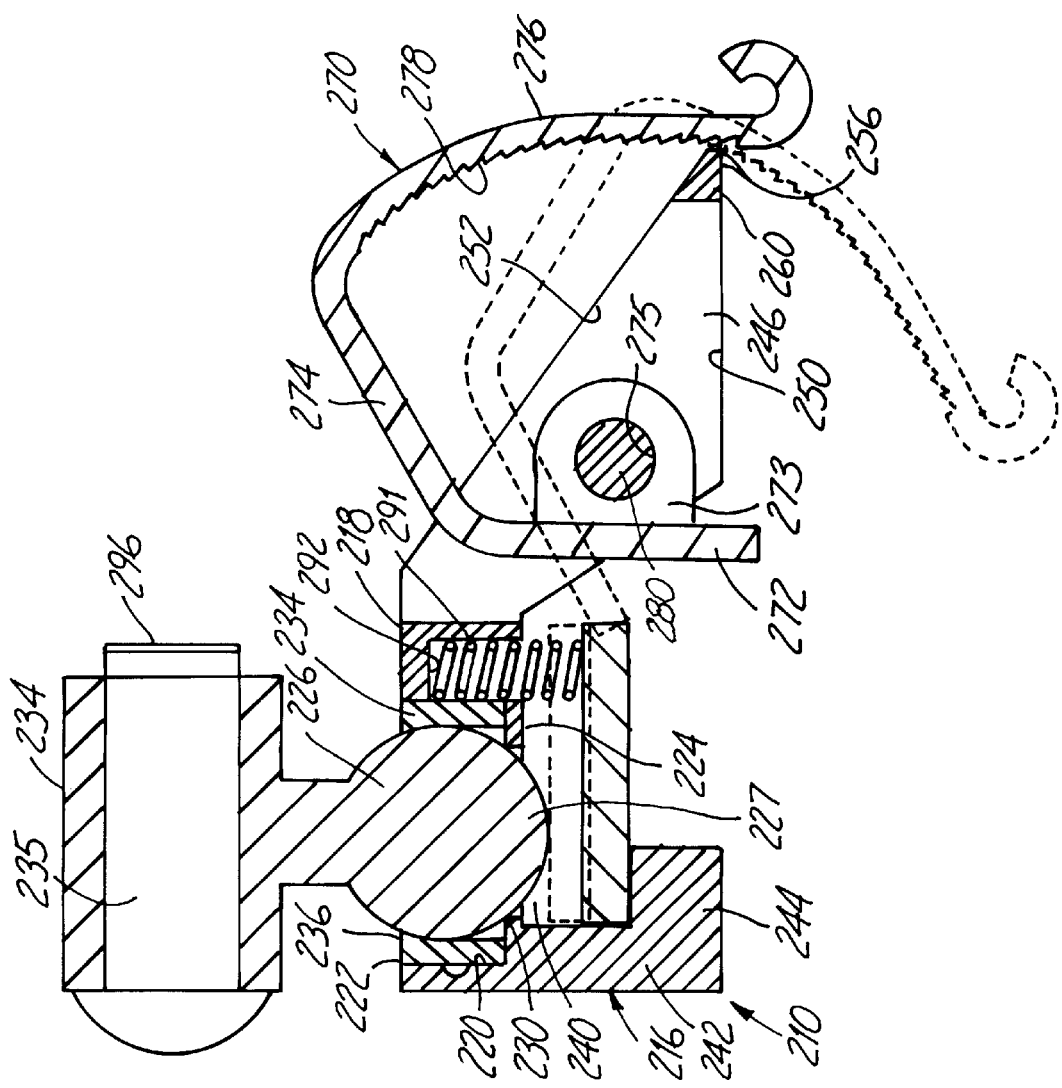
FIG. 6 is a sectional view of the second alternative embodiment of the clamping device of the present invention.

Referring to FIGS. 5 and 6, an alternative embodiment of the retractor clamp 210 of the present invention includes a spherical member 226 rotatably engaging a main body 216 of a retractor clamp 210. Attached to an exterior surface of the spherical member 226 is a retractor handle engaging member 234 having a through bore 235 which has four square corners 38 and side surfaces 40 having arcuate mid-portions as best illustrated in FIG. 7. The through bore 235, having four square corners 38 and side surfaces 40 having arcuate mid-portions, accepts both square cross-sectional retractor handles and circular cross-sectional retractor handles.

The main body 216 of the retractor clamp 210 includes a top portion 218 having a through bore 220. The through bore 220 has a first diameter at a top surface 222 of the top portion 218 and a second diameter at a bottom surface 224 of the top portion 218. The first and second diameters create a shoulder 230 in the through bore 220. The spherical member 226 is positioned with in the through bore 220 and rests on the shoulder 230. A portion 227 of the spherical member 226 extends beyond the bottom surface 224 of the top portion 218.

A securing member 234, positioned about the spherical member 226 and within the through bore 220, includes a swage 236 at an upper end which retains the spherical member 226 in the top portion 218 while allowing the spherical member 226 to rotate. The securing member 234 is preferably welded into the top portion 218 of the main body 216.

The main body 216 includes a C-shaped slot 240 proximate a first end 238 which engages a rectangular cross-sectional support arm 212. The C-shaped slot 240 is defined by the top portion 218, a back portion 242 and a bottom portion 244. One skilled in the art will recognize that the portion 227 of the spherical member 226 extending beyond the bottom surface 224 of the top portion 218 extends into the C-shaped slot 240.

First and second angled side portions 246, 248, respectively, extend from the edges of the top portion 218. The first and second angled portions 246, 248 have a flat bottom surface, one of which is shown at 250, and angled top surfaces 252, 254 where the angled top surfaces 252, 254 and the flat bottom surfaces 250, (not shown) converge at a point 256, 258 at a second end 239 of the main body 216. The points 256, 258 of the first and second angled side portions 246, 248 are joined by a cross member 260 also having the same pointed configuration.

The first and second angled side members 246, 248 also have through holes, one of which is shown at 262, which are aligned. A clamping member 270 is disposed between the first and second angled side members 246, 248. The clamping member 270 is generally U-shaped having a flat first portion 272. Extending from the flat first portion 272 are first and second tab members one of which is shown at 273, having aligned apertures one of which is shown at 275. The apertures within the first and second tabs 273, (not shown) align with the apertures 262, (not shown) in the first and second angled side members 246, 248 such that a pin 280 inserted through the apertures pivotally connects the clamping member 270 to the main body 216.

An angled portion 274 extends from the flat first portion 222 of the clamping member 270. Extending from the angled portion 274 is an arcuate portion 276 having angled teeth 278 along an inner surface of the arcuate portion 276. The angled teeth 278 cooperate with the cross member 260 of the main body 216 to secure the clamping member 270 in a selected position.

In operation, the clamp 210 is positioned on the support arm 212 by positioning the C-shaped slot 240 about the support arm 212. The support arm 212 contacts the spherical member 226 and is also biased downward by a compression spring 291 retained in a cavity 292 in the upper portion 218 as illustrated in FIG. 6. The clamping member 270 is positioned into a first position such that the flat first portion 272 is displaced from the support arm 212 thereby allowing the clamp 210 to be positioned on the support arm 212 and the spherical member 226 to be rotated within the main body 216.

When the clamp 210 is in selected position on the support arm 212 and the spherical member 226 is in a selected position within the main body 216 of the clamp 210, the clamping member 270 is rotated about the pin 280 and into a second position as shown in dotted lines in FIG. 6. As the clamping member 270 is being rotated into the second position the flat first portion 272 engages the bottom surface 213 of the rectangular cross-sectional support arm 212. As the clamping member 270 is further rotated about the pin 280, the first flat portion 272 forces the support member 212 into the portion 227 of the spherical member 226 disposed within the C-shaped slot 240. As the clamping member 272 further rotates, the first flat portion 272 applies a greater force to the support member 212 resulting in the spherical member 226 being in a first frictional engagement with the swage 236 and the top surface 211 of the support arm 212. Furthermore, the teeth 278 on the inner surface of the arcuate portion 276 of the clamping member 270 which engage the pointed cross member 260, retain the clamp 210 in a desired position by a second frictional engagement of the support arm 212 between the first flat portion 272 and the spherical member 226.

A retractor handle, as illustrated in FIGS. 1 and 2 at 60 and having teeth 62 along a length of the handle 60, is inserted into the through bore 235 in the retractor handle engaging member 234. Referring to FIGS. 5 and 6, a pawl 290, biased by a compression spring (not shown), engages the teeth 62 thereby preventing the retractor 61 from moving in an opposite direction. The pawl 290 is pivotally connected to the retractor handle engaging member 234 by a pin 292 extending through a first tab 294 and a through bore (not shown) along a side member 297 of the engaging member 234 and a second tab (not shown). To reverse the movement of the retractor handle 62 within the engaging member 234, a force is applied to the pawl 290 which overcomes the force provided by the spring (not shown) on the pawl 290 thereby disengaging the end 296 of the pawl 290 from the teeth 62 of the retractor handle 60.

The clamping member 270 has spring characteristics whereby the operator of the clamp 210 can pull outwardly away from the pointed cross member 260 to disengage the teeth 278 from the pointed cross member 260. With the teeth 278 disengaged from the pointed cross member 260, the clamping member 270 is rotated in the opposite direction, thereby allowing the clamping member 270 to disengage the bottom surface 213 of the support arm 212.

When the rotation of the clamping member 270 is reversed resulting in the clamping member 270 being rotated from the second position to the first position, the force provided by the clamping member 270 is removed thereby allowing the support arm 212 to disengage the spherical member 226. The spherical member 226 is then rotatable within the main body 216 of the clamp 210 and the clamp 210 is positionable on the support arm 212.

Figure 8:
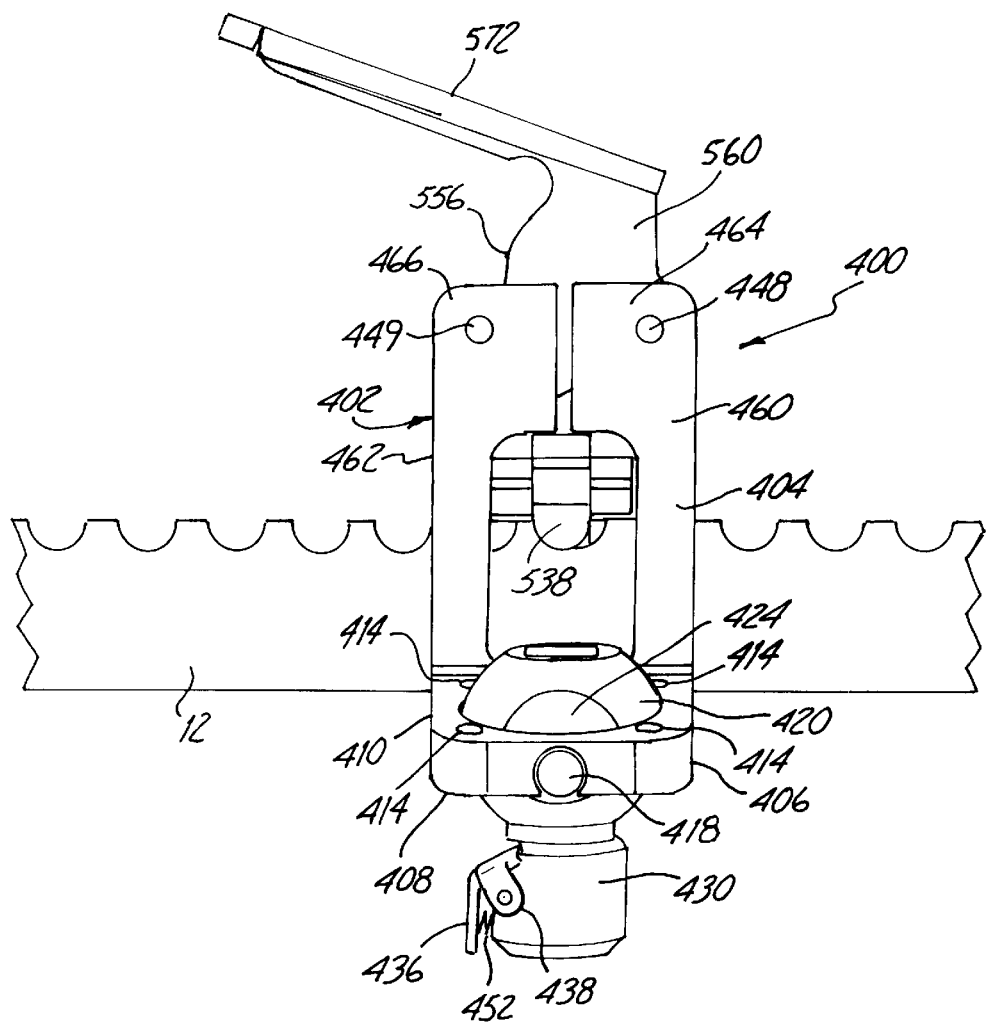
FIG. 8 is a top view of a third alternative embodiment of the clamping device of the present invention in a slidable engagement with a support arm.
Figure 9:
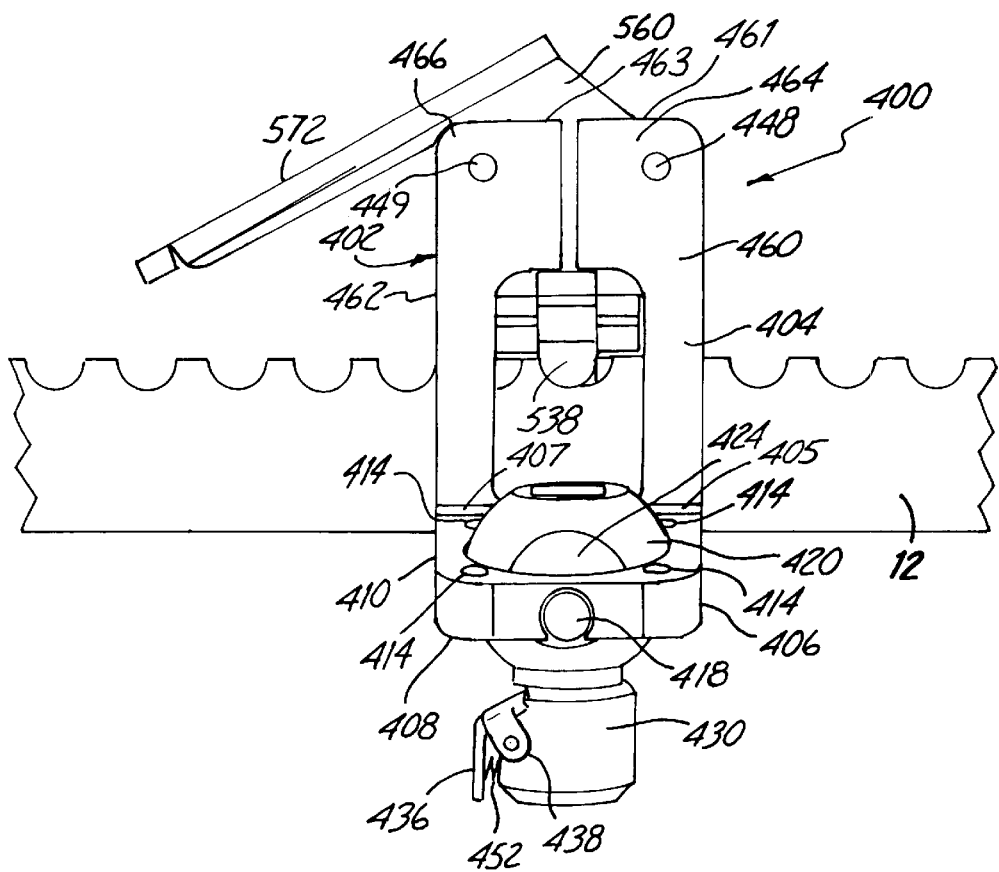
FIG. 9 is a top view of the third alternative embodiment of the clamping device of the present invention in a clamping position on the support arm.

In another alternative embodiment and the preferred embodiment, a clamping device is generally illustrated at 400 in FIGS. 8 and 9. The clamping device 400 engages a rectangular cross-sectional support arm 12 and provides for a retractor blade adjustment in three dimensions.

Referring to FIGS. 8–11, the clamping device 400 of the present invention includes a housing 402 having a main body 404 having a spherical member engaging portion 406 which cooperates with a spherical member 420. The spherical member retaining portion 406 includes a first side 408 having an aperture 412 extending therethrough to a second side 410. A diameter of the aperture 412 at the first side is smaller than a diameter of the spherical member 420 thereby preventing the spherical member 420 from exiting the aperture 412 from the first side 408. A diameter of the aperture 412 at the second side 410 of the spherical member retaining portion 406 is larger than the diameter of the spherical member 420 thereby allowing the spherical member 420 to be disposed within the aperture 412.

With the spherical member 420 disposed within the aperture 412, the spherical member 420 is rotatably captivated within the aperture 412 by decreasing the diameter of the aperture 412 at the second side 410 to be smaller than the diameter of the spherical member 420. Preferably, the diameter of the aperture 412 at the second side 410 is reduced by providing a plurality of bores 414 proximate the aperture 412. A punch tool (not shown) having a diameter greater than the diameter of the plurality of bores 414 is used to force material between each of the plurality of bores 414 and the aperture 412 into the aperture 412 thereby reducing the diameter at the second side 410. The reduction of the diameter of the aperture 412 at the second side 410 capti- vates the spherical member 420 within the aperture 412. Preferably, the second side 410 includes four bores 414 which are disposed at ninety degree angles from each other.

The spherical member 420, positioned within the aperture 412, includes a cavity 424 in an upper region 422 which cooperates with a pin 418 disposed through a top cut out portion 486 in a top region 407 of the spherical member retaining portion 406. The pin 418 extends into the cavity 424 in the upper region 422 of the spherical member 420 thereby limiting the rotation of the spherical member 420 within the aperture 412. A head 417 of the pin 418 has a larger diameter than the top cut out portion 486 such that the head 417 retains the pin 418 in the top cut out portion 486 while allowing a shaft 419 of the pin 418 to move within the top cut out portion 486 as best illustrated in FIGS. 10 and 11.

A retractor handle engaging member 430 is positioned within a complimentary through bore 426 in the spherical member 420 and is secured therein, preferably by a weld, as best illustrated in FIG. 11. The retractor handle engaging member 430 includes a through bore 432.

Referring to FIG. 7, the through bore 432 includes the same through bore as the other embodiments having four square corners 38 and side members 40 having arcuate mid-portions. The through bore 432 having four square corners 38 and side members 40 having arcuate mid-portions, allows the retractor handle engaging member 430 to accept both square cross-sectional retractor handles and circular cross-sectional retractor handles.

Figure 10:
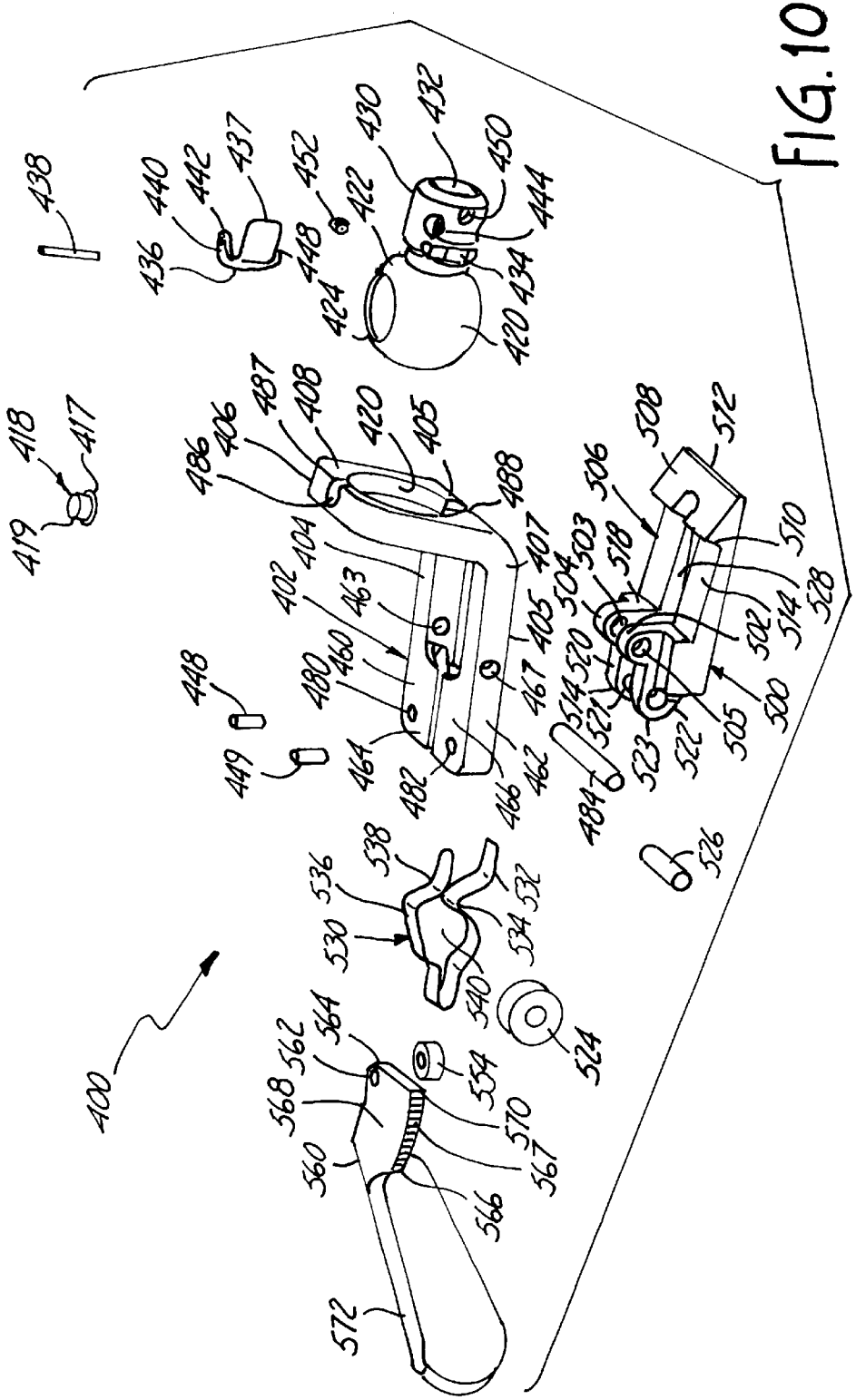
FIG. 10 is an exploded perspective view of the third alternative embodiment of the present invention.

Referring to FIGS. 10 and 11, the retractor handle engaging member 430 also includes a slot 434 which intersects the through bore 432. A pawl 436 is pivotally attached to the retractor handle engaging member 430 by a pin 438 disposed through an aperture 442 within a first ear 440 of the pawl 436, a through bore 444 in a side of the retractor handle engaging member 430 and a second aperture 446 within a second ear 448. The retractor handle engaging member 430 also includes an indention 450 which accepts a coil spring 452. The coil spring 452 biases the pawl 436 such that an end 437 of the pawl 436 is disposed through the slot 434 and within the through bore 432 in the retractor handle engaging member 430.

A retractor handle 61 having aligned slanted teeth 62 along a length of the handle 61, as best illustrated in FIGS. 1 and 2, is disposed within the through bore 432 in the retractor handle engaging member 430. The end 437 of the pawl 436 cooperates with the slanted teeth 62 to allow the retractor handle 61 to be inserted into the through bore 432 while preventing the retractor handle 61 from being removed from the through bore 432. The retractor handle 61 is removed from the through bore 432 by overcoming the bias of the spring 452 to position the end 437 of the pawl 436 outside of the through bore 432 thereby disengaging the pawl 436 from the slanted teeth 62 of the retractor handle 61.

Referring to FIGS. 8–11, the main body 404 of the housing 402 includes first and second leg members 460, 462 extending from first and second bottom edges 405, 407, respectively, of the spherical member retaining portion 406 such that the first and second leg members 460, 462 are spaced apart. Extending inwardly from distal ends 461, 463 of the first and second legs 460, 462 are first and second tabs 464, 466, all respectively. The first and second tabs 464, 466 each include top portions 468, 472 and bottom portions 470, 474 which are separated by a slot 476, 478, all respectively. Each tab 464, 466 also includes a set of aligned apertures 480, 482, respectively, in the top and bottom portions which intersect the slots 476, 478 wherein each set of the aligned apertures 480, 482 is adapted to receive a pin.

The first leg member 460 includes a first through hole 465 between the first tab 464 and the spherical member retaining portion 406. The second leg member 462 includes a second through hole 467 between the second tab 466 and the spherical engaging portion 406 wherein the first and second through holes 465, 467 are aligned to accept a shaft 484.

The first side 408 of the spherical member retaining portion 406 includes top and bottom cut out portions 486, 488, respectively along a vertical axis of the spherical member retaining portion 406. The top cut out portion 486 includes an opening 487 which is smaller than the diameter of the top cut out portion 486 such that the pin 418 is retained within the top cut out portion 486. One skilled in the art will recognize that the pin 418 must be retained within the top cut out portion 486 while allowing the diameter of the top cut out portion 486 to be manipulated. The bottom cut out portion 488 is vertically aligned with the top cut out portion 486 along the vertical axis of the spherical member retaining portion 406 thereby allowing the spherical member retaining portion 406 to flex at the bottom and top cut out portions 486, 488 and manipulate the diameter of the aperture 412 at the first side 408.

Referring to FIGS. 10 and 11, a retaining member 500 is pivotally attached to the housing 402 by the shaft 484 disposed through the first and second through holes 465, 467 in the first and second leg members 460, 462 and first and second though holes 503, 505 in first and second tabs 502, 504, respectively, extending from the retaining member 500.

The retaining member 500 includes an opening 506 defined by the vertical surface 510 of a ramped portion 508 proximate a first end 512, a flat portion 516 and a back portion 518. The opening 506 is designed to cooperate with the rectangular cross-sectional support member 12 to slidably secure the clamping device 400 to the support member 12.

Extending from a second end 514 of the retaining member 500 are first and second tabs 520, 522 having first and second apertures 521, 523, respectively. A spacer 524 is positioned between the first and second tabs 520, 522 such that a pin 526, disposed through the first aperture 521, the spacer 524 and the second aperture 523, rotatably retains the spacer 524 between the first and second tabs 520, 522.

A flat spring 530 is disposed about the spacer 524 and is positioned in a slot 528 in the retaining member 500. A bottom portion 532 of the flat spring 530 has a raised portion 534 and a top portion 536 of the flat spring 530 has a downwardly curved end 538 which define a pocket 540. The pocket 540 of the flat spring 530 cooperates with the spacer 524 to retain the flat spring 530 about the spacer 524.

A lever 560 is pivotally attached to the first tab 464 of the first leg member 460 by a pin 448 disposed through the aligned aperture 480 in the first tab 464 and an aperture 562 in the lever 560. A roller 554 is positioned in alignment with the second set of aligned apertures 482 in the second tab 466 of the second leg member 462, such that a pin 449 disposed through the second set of aligned apertures 482 and the roller 554 retains the roller 554 about the pin 449.

The lever 560 includes a camming surface 566 in relation to the pivotal attachment of the lever 560 to the first tab 464 which hereinafter will be referred to as the pivot point 564. What is meant by a camming surface 566 is an increase in the distance from the pivot point 564 to an edge of the lever 560. In addition to providing the camming surface 566, the lever 560 also includes a wedge 570 from an interior region 568 to the camming surface 566. A thickness of the lever 560 reduces from the interior region 568 to the edge of the camming surface 566 to define the wedge 570. A handle 572 is attached to the lever 560 to provide leverage in positioning the lever 560 into selected positions.

The lever 560 is positionable in a first position wherein the camming surface 566 does not contact the roller 554, the narrow portion of the wedge 570 contacts the flat spring 530 allowing the clamping device 400 to be removed from the support arm 12 and the spherical member 420 is rotatable within the spherical member retaining portion 406. The lever 560 is also positionable into a second position wherein the camming surface 566 contacts the roller 554 and a thicker middle portion of the wedge 570 contacts the flat spring 530 such that the clamping device 400 is slidably positionable on the support arm 12, but cannot be disposed from the retractor arm 12 and the spherical member 420 is rotatable within the spherical member retaining portion 406. The lever 560 is also positionable into a third position wherein the camming surface 566 exerts a force on the roller 554 and the thick portion of the wedge 570 contacts the flat spring 530 such that the clamping device 400 is fixed into a first selected position on the support arm 12 and the spherical member 420 is fixed into a second selected position within the spherical member retaining portion 406.

With the lever 560 in the first position, the camming surface 566 is disposed from the roller 554 and the narrow portion of the wedge 570 contacts the flat spring 530 on the second end 514 side of the pin 526. With the lever 560 in the first position, a gap between the ramp portion 508 of the retaining member 500 and a bottom surface 405 of the main body 404 of the housing 402 is greater than the thickness of the support arm 12 thereby allowing the clamping device 400 to be positioned onto and removed from the support arm 12. Additionally, the spherical member 420 is rotatable within the aperture 412 when the lever 560 is in the first position.

The lever 560 is positioned into the second position, as illustrated in FIG. 8, by pivoting the handle 572 toward the second leg member 462 of the main body 404 of the housing 402. As the lever 560 is rotated into the second position, the thickness of the wedge 570 contacting the top portion 536 of the flat spring 530 increases and thereby exerts a downward force on the flat spring 530 on the second end 514 side of the pivot pin 526. The downward force on the flat spring 530 on the second end 514 side of the pivot pin 526 causes a first end 514 of the retaining member 500 to rise and thereby reduce the gap between the bottom surface 405 of the main body 404 of the housing 402 and the top of the ramp portion 508. Raising the first end 512 of the clamping member 500 reduces the gap between the ramp portion 508 and the bottom surface 405 of the main body 404 of the housing 402 resulting in the clamping device 400 being slidably attached to the support arm 12 because the thickness of the support arm 12 is greater than the gap between the bottom surface 405 of the main body 404 of the housing 402 and the top of the ramp portion 508.

Referring to FIGS. 10 and 11, an indention 567 in the camming surface 566 contacts the roller 554 when the lever 560 is in the second position. Although the indention 567 is not necessary for the lever 560 to be positioned into the second position, the indention 567 aids in retaining the lever 560 in the second position as the clamping device 400 is slidably positioned on the support arm 12.

When the clamping device 400 is positioned into a first selected position and the spherical member 420 is positioned into a second selected position, the lever 560 is rotated into the third position, as illustrated in FIG. 9. As the lever 560 is rotated into the third position, the distance from the pivot point 564 to a contact point of the camming surface 566 with the roller 554 increases. As the distance from the pivot point 564 to the contact point increases, a force is applied to the roller 554 such that the first and second leg members 460, 462 are forced apart. As the first and second leg members 460, 462 are forced apart, the spherical member retaining portion 406 flexes at the top and bottom cut out portions 486, 488, respectively. The flexing at the top and bottom cut out portions 486, 488 causes the diameter of the aperture 412 at the first side 408 of the spherical member retaining portion 406 to decrease. The decrease in the diameter of the aperture 412 at the first side 408 causes a frictional engagement of the spherical member 420 with the spherical member retaining portion 406. The frictional engagement of the spherical member 420 with the spherical member retaining portion 406 fixes the spherical member 420 in the selected position.

As the spherical member 420 is being fixed into the selected position, the wedge 570 of the lever 560 creates a greater downward force on the retaining member 500 at the second end 514 side of the pin 526. The greater force causes the ramp portion 508 to raise further such that the bottom surface 405 of the main body 404 of the housing 402 and the flat portion 516 of the retaining member 500 contact an upper surface and a lower surface of the support arm 12.

The increased force on the flat spring 530 causes the top portion 536 of the flat spring 530 to be forced downward. The downward force in turn causes the end 538 of the top portion 536 to move toward the support arm 12 and creating a frictional engagement between a flat vertical surface 510 of the ramp portion 508 and the end 538 of the top portion 536 of the flat spring 530 with the support arm 12. The engagement of the flat vertical surface 510 of the ramp portion 508 and the end 538 of the top portion 536 of the flat spring 530 with the support arm 12 is effective in retaining the clamping device 400 to the support arm 12 having cut out portions, as illustrated in FIGS. 8 and 9, into which the end 538 of the top portion 536 of the flat spring 530 is inserted where the distance of each individual cut out portion limits the movement of the clamping device 400.

Although it is preferred to use the clamping device 400 of the present invention with a support arm 12 with cut out portions along the length of the support arm 12, one skilled in the art will recognize that the clamping device 400 of the present invention is also effectively used with a rectangular cross-sectional support arm 12 have smooth edges wherein the frictional engagement of the end 538 of the top portion 536 of the flat spring 530 and the vertical surface 510 of the ramp portion 508 with the support arm 12 retains the clamping device 400 in the selected position.

The depth of the retractor blade 63 attached to the shaft 61 having slanted teeth 62 along a length thereof is adjusted within the through bore 432 in the retractor handle engaging member 430 by the cooperation of the slanted teeth 62 with the end 437 of the pawl 436 where the end 437 of the pawl 436 prevents the retractor shaft 61 from moving in an opposite direction. To reposition the depth of the retractor blade 63, a force is applied to the pawl 436 to overcome the bias of the coil spring 452 and displace the end 437 of the pawl 436 from the through bore 432 thereby allowing the repositioning of the retractor shaft 61 within the through bore 432.

To reposition either the spherical member 420 within the spherical member retaining portion 406 or reposition the main body 404 of the clamping device 400 on the support arm 12, the lever 560 is repositioned into the second position. When the lever 560 is repositioned into the second position, the distance from the pivot point 564 to the contact point on the camming surface 566 with the roller 554 is decreased such that the first and second leg members 460, 462 of the main body 404 are in a relaxed state and the diameter of the aperture 412 at the first side 408 of the spherical member retaining portion 406 is increased which allows the spherical member 420 to freely rotate within the aperture 412. Additionally, the force on the flat spring 530 is reduced by contacting a narrower portion of the wedge 570 with the flat spring 530 such that the frictional engagement of the flat spring 530 and the vertical edge 510 of the ramp portion 508 with the support arm 12 is removed.

To remove the clamping device 400 from the support arm 12, the lever 560 is repositioned into the first position. Positioning the lever 560 into the first position increases the gap between the bottom surface 504 of the main body 404 of the housing 402 and the top of the ramp portion 408 such that the gap is greater than the thickness of the support arm 12 thereby allowing the clamping device 400 to be disposed from the support arm 12.

Although the present invention has been described with reference to preferred embodiments, workers skilled in the art will recognize that changes may be made in form and detail without departing from the spirit and scope of the invention.

What is claimed is:

1. A device for securing a retractor, to a rectangular cross-sectional support arm, the retractor having a handle and a blade, the device comprising:

a housing comprising a main member and a retaining member, the retaining member being operably attached to the main member wherein the main member and the retaining member cooperate to engage the support arm and wherein the main member further comprises a spheroidal member retaining portion comprising a surface defining an aperture wherein the surface defining the aperture includes a substantially uninterrupted circumference;

a spheroidal member disposed within the surface defining the spheroidal member retaining portion, the spheroidal portion being rotatably captivated therein, the spheroidal member having a through bore, the through bore adapted to engage the handle of the retractor; and a tightening mechanism operably attached to the main member and in communication with the spheroidal member retaining portion wherein the tightening mechanism is positionable between a first position wherein the spheroidal member is rotatable within the spheroidal member retaining portion and a second position wherein the tightening mechanism causes the substantially uninterrupted circumference of the surface defining the aperture to constrict such that the surface defining the aperture engages a substantially complete circumference of the spheroidal member resulting in a first frictional engagement of the spheroidal member with the spheroidal member retaining portion of the main member such that the spheroidal member is fixed in a first selected position.

2. The device of claim 1 wherein the spheroidal member retaining portion further comprises:

the portion having a first side and a second side and the aperture extending from the first side to the second side, the aperture having a diameter less than a diameter of the spheroidal member at the first side and at the second side and the aperture having a diameter greater than the diameter of the spheroidal member therebetween wherein the spheroidal member is rotatably captivated therein; and a top cut out portion and a bottom cut out portion along the first side such that the spheroidal retaining portion flexes.

3. The device of claim 2 wherein the main body further comprises:

a first leg extending from a first side of the spheroidal member retaining portion; and a second leg extending from a second side of the spheroidal member retaining portion, the first leg spaced apart from the second leg.

4. The device of claim 3 and further comprising the tightening mechanism pivotally attached to the first leg wherein the tightening mechanism comprises a camming surface wherein the camming surface creates a force between and separates the first and second legs when the tightening mechanism is positioned into the second position resulting in the flexing of the spheroidal member retaining portion at the top and bottom cut out portion such that a diameter of the aperture at the first side is reduced and frictionally engages the spheroidal member.

5. The device of claim 4 wherein the tightening mechanism further comprises a wedge wherein the wedge forces the retaining member into an engagement with the support arm.

6. The device of claim 5 wherein the retaining mechanism further comprises:

a spacer rotatably attached to the retaining member; and a flat spring disposed over the spacer and retained thereabout wherein the spacer includes a top portion having a downwardly curved end wherein when the wedge portion of the tightening mechanism contacts the spring member when the tightening mechanism is in the second position such that the end of the flat spring is forced into the support arm creating a frictional engagement between the flat spring and the retaining member.

7. The device of claim 4 wherein the camming surface of the tightening mechanism further comprises an indention wherein when the indention contacts the second leg of the main body and is retained in the selected position and wherein the intermediate thickness of the wedge communicates with the retaining mechanism to slidably retain the housing on the support arm and the spheroidal member is rotatable within the spheroidal member retaining portion.

8. The device of claim 2 and further comprising a pin wherein the pin extends from the top cut out portion in the spheroidal member retaining portion and into the aperture.

9. The device of claim 8 wherein the spheroidal member further comprises a surface defining a cavity wherein the pin is disposed within the surface defining the cavity of the spheroidal member and wherein the pin limits a rotational movement of the spheroidal member within the aperture of the spheroidal member retaining portion.

10. The device of claim 1 and further comprises a pawl operably connected to the spheroidal member wherein an end of the pawl intersects the through bore within the spheroidal member.

11. The device of claim 10 wherein the spheroidal member further comprises a slot wherein the slot intersects the through bore and wherein the end of the pawl disposes into the through bore through the slot.

12. The device of claim 11 where a spring biases the pawl such that the end of the pawl is biased into the through bore of the spheroidal member.

13. The device of claim 1 wherein a surface defining the through bore in the spheroidal member comprises four side surfaces defining four right corners which receive a square cross-sectional retractor handle and wherein a middle portion of each of the side surfaces has an arcuate convex surface which receive a circular cross-sectional retractor handle.

14. A device for securing a retractor to a rectangular cross-sectional support arm, the retractor having a handle and a blade, the device comprising:

a housing comprising a main member and a retaining member, the retaining member being operably attached to the main member wherein the main member and the retaining member cooperate to engage the support arm and wherein the main member further comprises a spheroidal member retaining portion wherein the spheroidal member retaining portion is of a unitary construction;

a spheroidal member disposed within the spheroidal member retaining portion such that the spheroidal member retaining portion contacts a substantially complete circumference of the spheroidal member, the spheroidal portion being captivated therein, the spheroidal member having a through bore, the through bore adapted to engage the handle of the retractor; and a tightening mechanism operably attached to the main member and in communication with the retaining member wherein the tightening mechanism is positionable between a first position wherein the housing is movable on the support arm and a second position wherein the tightening mechanism causes a first frictional engagement between the retaining member and the main member with the support arm such that the housing is fixed in a first selected position.

15. The device of claim 14 and further comprising:

the spheroidal member being rotatable within the spheroidal member retaining portion when the tightening mechanism is in the first position; and the spheroidal member being fixed in a second selected position by a frictional engagement between the spheroidal member and the spheroidal member retaining portion when the tightening mechanism is positioned in the second position.

16. The device of claim 15 wherein the spheroidal member retaining portion further comprises:

the portion having a first side and a second side and an aperture extending from the first side to the second side, the aperture having a diameter less than a diameter of the spheroidal member at the first side and at the second side and the aperture having a diameter greater than the diameter of the spheroidal member therebetween wherein the spheroidal member is rotatably captivated therein; and a top cut out portion and a bottom cut out portion along the first side such that the spheroidal retaining portion flexes.

17. The device of claim 16 and wherein the main member further comprises:

a first leg extending from a first side of the spheroidal member retaining portion; and a second leg extending from a second side of the spheroidal member retaining portion, the first leg spaced apart from the second leg.

18. The device of claim 17 and further comprising the tightening mechanism pivotally attached to the first leg wherein the tightening mechanism comprises a camming surface wherein the camming surface creates a force between and separates the first and second legs when the tightening mechanism is positioned into the second position resulting in the flexing of the spheroidal member retaining portion at the top and bottom cut out portion such that a diameter of the aperture at the first side is reduced and frictionally engages the spheroidal member.

19. The device of claim 18 wherein the tightening mechanism further comprises a wedge wherein the wedge forces the retaining member into an engagement with the support arm.

20. The device of claim 19 wherein the retaining member further comprises:
   a spacer rotatably attached to the retaining member; and
   a flat spring disposed over the spacer and retained thereabout wherein the spacer includes a top portion having a downwardly curved end wherein when the wedge of the tightening mechanism contacts the flat spring when the tightening mechanism is in the second position such that the end of the flat spring is forced into the support arm creating a frictional engagement between the flat spring and the retaining member.

21. The device of claim 19 wherein the camming surface of the tightening mechanism further comprises an indention wherein when the indention contacts the second leg of the main body and is retained in the selected position and wherein the intermediate thickness of the wedge communicates with the retaining member to slidably retain the housing on the support arm and the spheroidal member is rotatable within the spheroidal member retaining portion.

22. The device of claim 16 and further comprising a pin wherein the pin extends from the top cut out portion in the spheroidal member retaining portion and into the aperture.

23. The device of claim 22 wherein the spheroidal member further comprises a surface defining a cavity wherein the pin is disposed within the surface defining the cavity of the spheroidal member and wherein the pin limits rotational movement of the spheroidal member within the aperture of the spheroidal member retaining portion.

24. The device of claim 15 and further comprises a pawl operably connected to the spheroidal member wherein an end of the pawl intersects the through bore within the spheroidal member.

25. The device of claim 24 wherein the spheroidal member further comprises a slot wherein the slot intersects the through bore and wherein the end of the pawl disposes into the through bore through the slot.

26. The device of claim 25 where a spring biases the pawl such that the end of the pawl is biased into the through bore of the spheroidal member.

27. The device of claim 15 wherein a surface defining the through bore in the spheroidal member comprises four side surfaces defining four right corners which receive a square cross-sectional retractor handle and wherein a middle portion of each of the side surfaces has an arcuate convex surface which receive a circular cross-sectional retractor handle.

28. A clamp for securing a handle of a retractor, the handle having either a circular cross-section or a polygonal cross-section, the clamp comprising:
   a housing of a unitary construction having a through hole for accepting the handle of the retractor, the through hole having a cross-section defined by a plurality of straight lines forming a right angle or an obtuse angle separated by arcuate sections.

29. The clamp of claim 28 wherein the housing further comprises a main member and a retaining member, the retaining member being operably attached to the main member wherein the main member and the retaining member cooperate to engage a support arm and wherein the main member further comprises a spheroidal member retaining portion and wherein the clamp further comprises:
   a spheroidal member disposed within the spheroidal member retaining portion, the spheroidal portion being rotatably captivated therein, the spheroidal member having a through hole for receiving the handle of the retractor; and
   a tightening mechanism operably attached to the main member and in communication with the retaining member wherein the tightening mechanism is positionable between a first position wherein the spheroidal member is rotatable within the spheroidal member retaining portion and a second position wherein the tightening mechanism causes a first frictional engagement of the spheroidal member with the spheroidal member retaining portion of the main member such that the spheroidal member is fixed in a first selected position.

30. The clamp of claim 29 wherein the spheroidal member retaining portion further comprises:
   a first side and a second side and an aperture extending from the first side to the second side, the aperture having a diameter less than a diameter of the spheroidal member at the first side and at the second side and the aperture having a diameter greater than the diameter of the spheroidal member therebetween wherein the spheroidal member is rotatably captivated therein; and
   a top cut out portion and a bottom cut out portion along the first side such that the spheroidal retaining portion flexes.

31. The clamp of claim 30 and wherein the main body further comprises:
   a first leg extending from a first side of the spheroidal member retaining portion; and
   a second leg extending from a second side of the spheroidal member retaining portion, the first leg spaced apart from the second leg.

32. The clamp of claim 31 and further comprising the tightening mechanism being pivotally attached to the first leg wherein the tightening mechanism further comprises a camming surface wherein the camming surface creates a force between and separates the first and second legs when the tightening mechanism is positioned into the second position resulting in the flexing of the spheroidal member retaining portion at the top and bottom cut out portion such that a diameter of the aperture at the first side is reduced and frictionally engages the spheroidal member.

33. The clamp of claim 32 wherein the tightening mechanism further comprises a wedge wherein the wedge forces the retaining member into an engagement with the support arm.

34. The clamp of claim 33 wherein the retaining member further comprises:
   a spacer rotatably attached to the retaining member; and
   a flat spring disposed over the spacer and retained thereabout wherein the spacer includes a top portion having a downwardly curved end wherein when the wedge of the tightening mechanism contacts the flat spring when the tightening mechanism is in the second position such that the end of the flat spring is forced into the support arm creating a frictional engagement between the flat spring and the retaining member.

35. The clamp of claim 32 wherein the camming surface of the tightening mechanism further comprises an indention wherein when the indention contacts the second leg of the main body and is retained in the selected position and wherein the intermediate thickness of the wedge communicates with the retaining member to slidably retain the housing on the support arm and the spheroidal member is rotatable within the spheroidal member retaining portion.

36. The clamp of claim 30 and further comprising a pin wherein the pin extends from the top cut out portion in the spheroidal member retaining portion and into the aperture.

37. The clamp of claim 36 wherein the spheroidal member further comprises a surface defining a cavity wherein the pin is disposed within the surface defining the cavity of the spheroidal member and wherein the pin limits rotational movement of the spheroidal member within the aperture of the spheroidal member retaining portion.

38. The clamp of claim 29 and further comprising a pawl operably connected to the spheroidal member wherein an end of the pawl intersects the through hole within the spheroidal member.

39. The clamp of claim 38 wherein the spheroidal member further comprises a slot wherein the slot intersects the through hole and wherein the end of the pawl disposes into the through bore through the slot.

40. The device of claim 39 where a spring biases the pawl such that the end of the pawl is biased into the through hole of the spheroidal member.

41. A clamp for use in a retractor support system, the retractor support system having first and second retractor support members, the clamp comprising:
  a spheroidal body attached to the first retractor support member;
  a housing wherein a portion of the housing of unitary construction continuously surrounds the spheroidal body along at least one circumferential plane and rotatably captivates the spheroidal body, the housing attachable to the second retractor support member; and
  a mechanism for bending the portion of the housing surrounding the spheroidal member such that the portion of the housing frictionally engages the spheroidal body sufficiently to retain the spheroidal body in a first selected position.

42. The clamp of claim 41 wherein the portion of the housing surrounding the spheroidal body comprises:
  a first side and a second side and an aperture extending from the first side to the second side, the aperture having a diameter less than a diameter of the spheroidal body at the first side and at the second side and the aperture having a diameter greater than the diameter of the spheroidal body therebetween wherein the spheroidal body is rotatably captivated therein;
  a top cut out portion in the first side along a vertical axis; and
  a bottom cut out portion in the first side along the vertical axis such that the cooperation of the top and bottom cut out portions allows the portion to bend.

43. The clamp of claim 42 wherein the housing further comprises:
  a main member and a retaining member, the retaining member being operably attached to the main member wherein the main member and the retaining member cooperate to engage the second support arm and wherein the main member further comprises the portion of the housing which rotatably captivates the spheroidal body; and
  a tightening mechanism operably attached to the main member and in communication with the retaining member wherein the tightening mechanism is positionable between a first position wherein the spheroidal body is rotatable within the portion of the housing and a second position wherein the tightening mechanism causes a first frictional engagement of the spheroidal body with the portion of the housing surrounding the spheroidal body such that the spheroidal body is fixed in the first selected position.

44. The clamp of claim 43 and wherein the main member further comprises:
  a first leg extending from a first side of the portion of the housing retaining the spheroidal body; and
  a second leg extending from a second side of the portion of the housing retaining the spheroidal body, the first leg spaced apart from the second leg.

45. The clamp of claim 44 and further comprising the tightening mechanism pivotally attached to the first leg wherein the tightening mechanism comprises a camming surface wherein the camming surface creates a force between and separates the first and second legs when the tightening mechanism is positioned into the second position resulting in the bending of the portion of the housing surrounding the spheroidal body at the top and bottom cut out portion such that a diameter of the aperture at the first side is reduced and frictionally engages the spheroidal body.

46. The clamp of claim 45 wherein the tightening mechanism further comprises a wedge wherein the wedge forces the retaining member into an engagement with the second support arm.

47. The clamp of claim 46 wherein the retaining mechanism further comprises:
  a spacer rotatably attached to the retaining member; and
  a flat spring disposed over the spacer and retained thereabout wherein the spacer includes a top portion having a downwardly curved end wherein when the wedge of the tightening mechanism contacts the flat spring when the tightening mechanism is in the second position such that the end of the flat spring is forced into the second support member creating a frictional engagement between the flat spring and the retaining member.

48. The clamp of claim 45 wherein the camming surface of the tightening mechanism further comprises an indention wherein when the indention contacts the second leg of the main body and is retained in the selected position and wherein the intermediate thickness of the wedge communicates with the retaining mechanism to slidably retain the housing on the second support member and the spheroidal body is rotatable within the portion of the housing captivating the spheroidal body.

49. The clamp of claim 42 and further comprising a pin wherein the pin extends from the top cut out portion in the portion of the housing captivating the spheroidal body and into the aperture.

50. The clamp of claim 49 wherein the spheroidal body further comprises a surface defining a cavity wherein the pin is disposed within the surface defining the cavity of the spheroidal body and wherein the pin limits a rotational movement of the spheroidal body within the aperture of the portion of the housing captivating the spheroidal body.

51. A method of positioning a retractor blade in three dimensions within a surgical site, the retractor blade having a retractor handle operably attached thereto, the retractor handle operably attached to a retractor holder, the method comprising:
  disposing the retractor holder on a support member, the retractor holder having a spheroidal member rotatably attached to a main body of the retractor holder wherein the main body contacts a substantially complete circumference of the spheroidal member;

disposing the retractor handle through a through bore in the spheroidal member;

rotating the spheroidal member to adjust a vertical position and a horizontal position of the retractor blade; and adjusting a depth of the retractor blade by manipulating the retractor handle through the through bore in the spheroidal member.

52. The method of claim 51 and further comprising:

manipulating the main body of the retractor holder to frictionally engage the spheroidal member thereby fixing the horizontal position and the vertical position of the retractor blade.

53. The method of claim 52 wherein the manipulation of the main body comprises:

pivoting a lever having a camming surface, the lever attached to a first leg extending from a first edge of a spheroidal member retaining portion;

engaging the camming surface of the lever with a second leg extending from a second edge of the spheroidal member retaining portion; and forcing the first and second legs apart with the camming surface and thereby constricting a diameter of the spheroidal member retaining portion to secure the spheroidal member in the selected position.

54. The method of claim 53 wherein the adjusting of the depth of the retractor blade further comprises:

positioning the retractor blade at the selected depth by adjusting the position of the retractor handle within the through bore in the spheroidal member, the handle having aligned teeth along a length thereof; and retaining the retractor blade in the selected depth by engaging the aligned teeth with a pawl attached to the retractor holder.

55. The method of claim 54 and further comprising:

disengaging the pawl from the aligned teeth in the retractor handle;

repositioning the depth of the retractor blade; and re-engaging the pawl with the aligned teeth.

56. The method of claim 51 wherein the method of disposing the retractor holder on the support arm comprises:

engaging a retaining member operably attached to the main body of the retractor holder with a bottom surface of the support arm to retain the retractor holder on the support arm.

57. The method of claim 56 wherein the method of disposing the retractor holder on the support arm comprises:

engaging a spring member with the support arm to frictionally retain the retractor holder in the selected position on the support arm between the spring member and the retaining member.

58. A method of adjusting a position of a retractor blade within a surgical site, the method comprising:

disposing a retractor handle, the retractor handle operably attached to the retractor blade, through a through bore disposed through a spheroidal member, the spheroidal member rotatably attached to a main body of a retractor holder;

adjusting a horizontal position and vertical position of the retractor blade by rotating the spheroidal member within the main body of the retractor holder; and adjusting a depth of the retractor blade by manipulating a position of the retractor handle within the through bore disposed in the spheroidal member.

59. The method of claim 58 and further comprising:

securing the spheroidal member in selected position by a frictional engagement of the spheroidal member with the main body of the retractor holder.

60. The method of claim 59 and further comprising:

pivoting a lever having a camming surface, the lever attached to a first leg extending from a first edge of a spheroidal member retaining portion;

engaging the camming surface of the lever with a second leg extending from a second edge of the spheroidal member retaining portion; and forcing the first and second legs apart with the camming surface and thereby constricting a diameter of the spheroidal member retaining portion to secure the spheroidal member in the selected position.

61. The method of claim 58 and further comprising:

securing the retractor handle in a selected position by engaging a plurality of aligned teeth along a length of the retractor handle with a pawl operably attached to the retractor holder.

62. The method of claim 61 and further comprising:

disengaging the pawl from the plurality of aligned teeth in the handle;

repositioning the depth of the retractor blade; and re-engaging the pawl with the aligned teeth.

63. The method of claim 58 wherein the method of disposing the retractor holder on the support arm further comprises:

engaging a retaining member operably attached to the main body of the retractor holder with a bottom surface of a support arm to retain the retractor holder on the support arm.

64. The method of claim 63 wherein the method of disposing the retractor holder on the support arm further comprises:

engaging a spring member against the support arm to frictionally retain the retractor holder between the spring member and the retaining member such that the retractor holder is secured in the selected position on the support arm.

65. A device for securing a retractor, to a rectangular cross-sectional support arm, the retractor having a handle and a blade, the device comprising:

a housing comprising a main member and a retaining member, the retaining member being operably attached to the main member wherein the main member and the retaining member cooperate to engage the support arm and wherein the main member further comprises a spheroidal member retaining portion including a surface for frictional engagement;

a spheroidal member disposed within the surface for frictional engagement within the spheroidal member retaining portion, the spheroidal portion being rotatably captivated therein, the spheroidal member having a through bore, the through bore adapted to engage the handle of the retractor; and a tightening mechanism operably attached to the main member and in communication with the spheroidal member retaining portion and in communication with the retaining member wherein the tightening mechanism is positionable between a first position wherein the spheroidal member is rotatable within the spheroidal member retaining portion and a second position wherein the tightening mechanism causes the surface for frictional engagement to bend sufficiently such that the spheroidal member is frictionally retained in a first selected position.

66. The device of claim 65 wherein the surface for frictional engagement of the spheroidal member retaining portion further comprises:
   a first side and a second side and the surface extending from the first side to the second side, the surface having a diameter less than a diameter of the spheroidal member at the first side and at the second side and the surface having a diameter greater than the diameter of the spheroidal member therebetween wherein the spheroidal member is rotatably captivated therein; and
   a top cut out portion and a bottom cut out portion along the first side such that the spheroidal retaining portion bends.

67. The device of claim 66 wherein the main body further comprises:
   a first leg extending from a first side of the spheroidal member retaining portion; and
   a second leg extending from a second side of the spheroidal member retaining portion, the first leg spaced apart from the second leg.

68. The device of claim 67 and further comprising the tightening mechanism pivotally attached to the first leg wherein the tightening mechanism comprises a camming surface wherein the camming surface creates a force between and separates the first and second legs when the tightening mechanism is positioned into the second position resulting in the bending of the spheroidal member retaining portion at the top and bottom cut out portion such that the surface for frictional engagement at the first side is reduced and frictionally engages the spheroidal member.

69. The device of claim 68 wherein the tightening mechanism further comprises a wedge where the wedge forces the retaining member into an engagement with the support arm.

70. The device of claim 69 wherein the retaining member further comprises:
   a spacer rotatably attached to the retaining member; and
   a flat spring disposed over the spacer and retained thereabout wherein the spacer includes a top portion having a downwardly curved end wherein when the wedge of the tightening mechanism contacts the flat spring when the tightening mechanism is in the second position such that the end of the flat spring is forced into the support arm creating a frictional engagement between the flat spring and the retaining member.

71. The device of claim 68 wherein the camming surface of the tightening mechanism further comprises an indention wherein when the indention contacts the second leg of the main body and is retained in the selected position and wherein the intermediate thickness of the wedge communicates with the retaining member to slidably retain the housing on the support arm and the spheroidal member is rotatable within the spheroidal member retaining portion.

72. The device of claim 66 and further comprising a pin wherein the pin extends from the top cut out portion in the spheroidal member retaining portion and into the aperture.

73. The device of claim 72 wherein the spheroidal member further comprises a surface defining a cavity wherein the pin is disposed within the surface defining the cavity of the spheroidal member and wherein the pin limits a rotational movement of the spheroidal member within the aperture of the spheroidal member retaining portion.

74. The device of claim 68 and further comprises a pawl operably connected to the spheroidal member wherein an end of the pawl intersects the through bore within the spheroidal member.

75. The device of claim 74 wherein the spheroidal member further comprises a slot wherein the slot intersects the through bore and wherein the end of the pawl disposes into the through bore through the slot.

76. The device of claim 75 where a spring biases the pawl such that the end of the pawl is biased into the through bore of the spheroidal member.

77. The device of claim 65 wherein a surface defining the through bore in the spheroidal member comprises four side surfaces defining four right corners which receive a square cross-sectional retractor handle and wherein a middle portion of each of the side surfaces has an arcuate convex surface which receive a circular cross-sectional retractor handle.

78. A device for securing a retractor to a rectangular cross-sectional support arm, the retractor having a handle and a blade, the device comprising:
   a housing comprising a main member and a retaining member, the retaining member being operably attached to the main member wherein the main member and the retaining member cooperate to engage the support arm and wherein the main member further comprises a spheroidal member retaining portion comprising a surface defining an aperture wherein the surface defining the aperture includes a substantially uninterrupted circumference;
   a spheroidal member disposed within the surface defining the spheroidal member retaining portion, the spheroidal portion being rotatably captivated therein, the spheroidal member having a through bore, the through bore adapted to engage the handle of the retractor; and
   a tightening mechanism operably attached to the main and in communication with the spheroidal member retaining portion wherein the tightening mechanism is positionable between a first position wherein the spheroidal member is rotatable within the spheroidal member retaining portion and a second position wherein the tightening mechanism causes a first frictional engagement of a substantially complete circumference of the spheroidal member with the spheroidal member retaining portion of the main member such that the spheroidal member is fixed in a first selected position by bending the spheroidal member retaining portion.

79. The device of claim 78 wherein the spheroidal member retaining portion further comprises:
   the portion having a first side and a second side and the aperture extending from the first side to the second side, the aperture having a diameter less than a diameter of the spheroidal member at the first side and at the second side and the aperture having a diameter greater than the diameter of the spheroidal member therebetween wherein the spheroidal member is rotatably captivated therein; and
   a top cut out portion and a bottom cut out portion along the first side such that the spheroidal retaining portion bends.

80. The device of claim 79 wherein the main body further comprises:
   a first leg extending from a first side of the spheroidal member retaining portion; and
   a second leg extending from a second side of the spheroidal member retaining portion, the first leg spaced apart from the second leg.

81. The device of claim 80 and further comprising the tightening mechanism pivotally attached to the first leg wherein the tightening mechanism comprises a camming surface wherein the camming surface creates a force between and separates the first and second legs when the tightening mechanism is positioned into the second position resulting in the flexing of the spheroidal member retaining portion at the top and bottom cut out portion such that a diameter of the aperture at the first side is reduced and frictionally engages the spheroidal member.

82. The device of claim 81 wherein the tightening mechanism further comprises a wedge wherein the wedge forces the retaining member into an engagement with the support arm.

83. The device of claim 82 wherein the retaining member further comprises:

a spacer rotatably attached to the retaining member; and a flat spring disposed over the spacer and retained thereabout wherein the spacer includes a top portion having a downwardly curved end wherein when the wedge of the tightening mechanism contacts the flat spring when the tightening mechanism is in the second position such that the end of the flat spring is forced into the support arm creating a frictional engagement between the flat spring and the retaining member.

84. The device of claim 81 wherein the camming surface of the tightening mechanism further comprises an indention wherein when the indention contacts the second leg of the main body and is retained in the selected position and wherein the intermediate thickness of the wedge communicates with the retaining member to slidably retain the housing on the support arm and the spheroidal member is rotatable within the spheroidal member retaining portion.

85. The device of claim 80 and further comprising a pin wherein the pin extends from the top cut out portion in the spheroidal member retaining portion and into the aperture.

86. The device of claim 85 wherein the spheroidal member further comprises a surface defining a cavity wherein the pin is disposed within the surface defining the cavity of the spheroidal member and wherein the pin limits a rotational movement of the spheroidal member within the aperture of the spheroidal member retaining portion.

87. The device of claim 79 and further comprises a pawl operably connected to the spheroidal member wherein an end of the pawl intersects the through bore within the spheroidal member.

88. The device of claim 87 wherein the spheroidal member further comprises a slot wherein the slot intersects the through bore and wherein the end of the pawl disposes into the through bore through the slot.

89. The device of claim 88 where a spring biases the pawl such that the end of the pawl is biased into the through bore of the spheroidal member.

90. The device of claim 79 wherein a surface defining the through bore in the spheroidal member comprises four side surfaces defining four right corners which receive a square cross-sectional retractor handle and wherein a middle portion of each of the side surfaces has an arcuate convex surface which receive a circular cross-sectional retractor handle.

\* \* \* \* \*

UNITED STATES PATENT AND TRADEMARK OFFICE
CERTIFICATE OF CORRECTION

PATENT NO. : 6,602,190 B2
DATED : August 5, 2003
INVENTOR(S) : Walter Dobrovolny It is certified that error appears in the above-identified patent and that said Letters Patent is hereby corrected as shown below:

<u>Column 22,</u>
Line 32, after "main", insert -- member --.

Signed and Sealed this

Fifteenth Day of June, 2004

JON W. DUDAS
*Acting Director of the United States Patent and Trademark Office*